(12) United States Patent
Haraguchi

(10) Patent No.: US 10,238,271 B2
(45) Date of Patent: Mar. 26, 2019

(54) TRACTION BALANCE ADJUSTMENT MECHANISM, MANIPULATOR AND MANIPULATOR SYSTEM

(71) Applicant: OLYMPUS CORPORATION, Tokyo (JP)

(72) Inventor: Masafumi Haraguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 163 days.

(21) Appl. No.: 15/228,163

(22) Filed: Aug. 4, 2016

(65) Prior Publication Data

US 2016/0338571 A1 Nov. 24, 2016

Related U.S. Application Data

(63) Continuation of application No. PCT/JP2015/051781, filed on Jan. 23, 2015.

(30) Foreign Application Priority Data

Feb. 7, 2014 (JP) .................................. 2014-021991

(51) Int. Cl.
*A61B 1/00* (2006.01)
*A61B 1/005* (2006.01)
(Continued)

(52) U.S. Cl.
CPC ........ *A61B 1/0057* (2013.01); *A61B 1/00045* (2013.01); *A61B 1/0052* (2013.01);
(Continued)

(58) Field of Classification Search
CPC . A61B 1/0057; A61B 1/0052; A61B 1/00045; A61B 1/00087; A61B 1/05; A61B 1/06; B25J 9/104
See application file for complete search history.

(56) References Cited

U.S. PATENT DOCUMENTS 4,483,326 A * 11/1984 Yamaka ............... A61B 1/0057
600/141
5,904,667 A   5/1999 Falwell
(Continued)

FOREIGN PATENT DOCUMENTS

CN    202235277 U    5/2012
CN    102573599 A    7/2012
(Continued)

OTHER PUBLICATIONS

International Search Report dated Apr. 14, 2015 issued in PCT/JP2015/051781.
(Continued)

*Primary Examiner* — Timothy J Neal
(74) *Attorney, Agent, or Firm* — Scully, Scott, Murphy & Presser, P.C.

(57) ABSTRACT

The traction balance adjustment mechanism 1 includes a movable part 2 that goes into operation through at least one degree of freedom, wires 7 connected to the movable part 2, and a traction part 6 that pulls one of the wires 7 and pushes out the other, wherein the length of the one wire 7 pulled by the traction part 6 is longer than the length of the other wire 7 pushed out.

5 Claims, 11 Drawing Sheets

(51) Int. Cl.
*A61B 1/05* (2006.01)
*A61B 1/06* (2006.01)
*B25J 9/10* (2006.01)
*A61M 25/01* (2006.01)

(52) U.S. Cl.
CPC ............ *A61B 1/00087* (2013.01); *A61B 1/05* (2013.01); *A61B 1/06* (2013.01); *B25J 9/104* (2013.01); *A61M 25/0136* (2013.01); *A61M 25/0147* (2013.01)

(56) References Cited

U.S. PATENT DOCUMENTS

| | | | |
|---|---|---|---|
| 6,702,737 B2 * | 3/2004 | Hino | A61B 1/0052 600/146 |
| 2002/0143238 A1 | 10/2002 | Hino et al. | |
| 2007/0238925 A1 | 10/2007 | Lee et al. | |
| 2008/0275302 A1 | 11/2008 | Hosaka | |
| 2011/0295063 A1 | 12/2011 | Umemoto et al. | |
| 2012/0220832 A1 | 8/2012 | Nakade et al. | |

FOREIGN PATENT DOCUMENTS

| | | |
|---|---|---|
| JP | S56-116441 A | 9/1981 |
| JP | H02-053705 U | 4/1990 |
| JP | H08-082749 A | 3/1996 |
| JP | H09-75301 A | 3/1997 |
| JP | 2001128934 A | 5/2001 |
| JP | 2008-142199 A | 6/2008 |
| JP | 2011-143029 A | 7/2011 |

OTHER PUBLICATIONS

Extended Supplementary European Search Report dated Oct. 2, 2017 in European Patent Application No. 15 74 6278.9.

* cited by examiner

TRACTION BALANCE ADJUSTMENT MECHANISM, MANIPULATOR AND MANIPULATOR SYSTEM

CROSS-REFERENCE TO RELATED APPLICATIONS

This application is a continuation claiming priority on the basis of Japan Patent Application No. 2014-021991 applied in Japan on Feb. 7, 2014 and based on PCT/JP2015/051781 filed on Jan. 23, 2015. The contents of both the PCT application and the Japan Application are incorporated herein by reference.

BACKGROUND OF THE INVENTION AND RELATED ART STATEMENT

The present invention relates to a traction balance adjustment mechanism capable of adjusting balance in traction of wires through an apparatus which operates a distal-end member by pulling and letting out the wires, a manipulator and a manipulator system.

So far there has been a manipulator available in which the curving state of a distal-end portion is operated by pulling and letting out a wire. At the time when the wire is driven, there is an elongation of the wire on the pulling side. For this reason, as the wire is pulled and let out at the same stroke, it causes a slack in the wire on the let-out side, resulting possibly in defections such as deviation of the wire out of the pathway.

Japanese Patent Publication JP(A) 2008-142199 discloses that in order to prevent operating wires from slackening upon operation of a curving portion to make sure a good operational feeling, the center axis of the take-up portion of a pulley to which the base ends of operating wires are fixed is decentered with respect to the rotating center axis of the pulley.

SUMMARY OF INVENTION

The traction balance adjustment mechanism according to one embodiment of the invention including:
a movable part that operates through at least one degree of freedom,
power transmission members that are connected to the movable part, and
a traction part that pulls one of the power transmission members and pushes out the other, wherein the length of the one power transmission member pulled by the traction part is longer than the length of the other power transmission member pushed out.

The manipulator according to one embodiment including:
a driving part for driving the traction part,
an operating part for actuating the driving part to operate an orientation of the movable part, and
the traction balance adjustment mechanism.

The manipulator system according to one embodiment including:
the manipulator,
a system control unit for controlling the manipulator, and
a display unit for displaying an image acquired through the manipulator, wherein the manipulator includes an endoscope, and the system control unit is adapted to display an image acquired through the endoscope on the display unit.

DESCRIPTION OF EMBODIMENTS

Some embodiments of the invention will now be explained.

Figure 1:
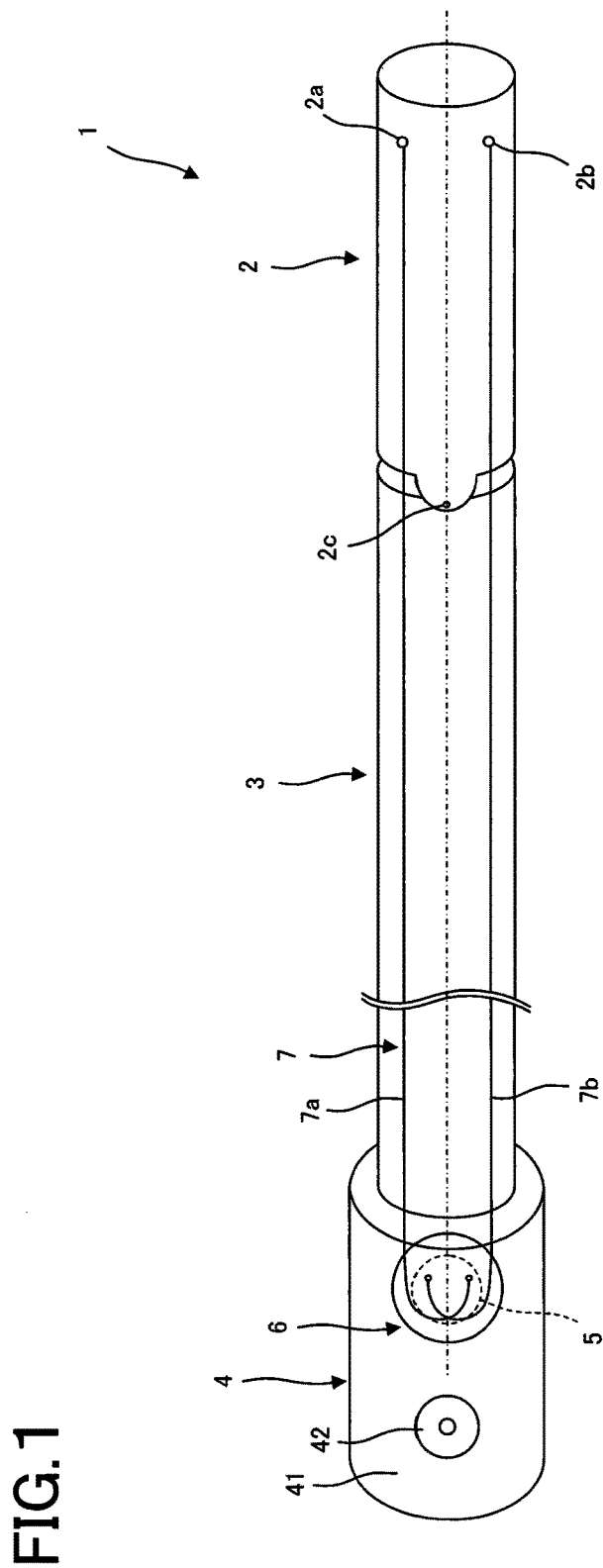
FIG. 1 is illustrative in schematic of the traction balance adjustment mechanism according to one embodiment of the invention.

FIG. 1 is a schematic view of the traction balance adjustment mechanism 1 according to one embodiment of the invention.

The traction balance adjustment mechanism 1 includes a movable part 2, a coupler 3, an operating part 4, a driving part 5, a traction part 6, and wires 7.

The movable part 2 is a tubular member that is rotatably mounted with an axial member 2c extending through the movable part 2 and coupler 3 as center. The movable part 2 includes wire mounts 2a and 2b to which one ends of the wires 7 are attached. The coupler 3 is a tubular member that couples the operating part 4 to the movable part 2 and has the wires 7 inserted inside.

The operating part 4 includes a grip 41 grasped by an operator, and an operation instruction portion 42 that is formed at the grip 41 and includes a joystick or the like for giving an instruction about the operation of the movable part 2.

While the grip 41 here is formed into a cylindrical shape, it may be configured into any desired easy-to-grasp shape. The operation instruction portion 42 is designed such that a protruding rod-form lever is tilted down, as is the case with a joystick using a potentiometer, to bend the movable part 2 in the tilting-down direction. Note here that a pointing device, a touchpad or the like may be used for the operation instruction portion 42.

The driving part 5 is built in the grip 41 of the operating part 4. The driving part 5 includes an actuator or the like adapted to drive the traction part 6, to which the other end of the wires 7 is attached, to enable the wires 7 to be pulled and let out.

It is here to be noted that the driving part 5 is incorporated together with the traction part 6 in the coupler 3, and a motor or the like that enables the wires 7 to be wound around or let out from the traction part 6 may be used for the actuator that forms part of the driving part 5 of the first embodiment.

Figure 2:
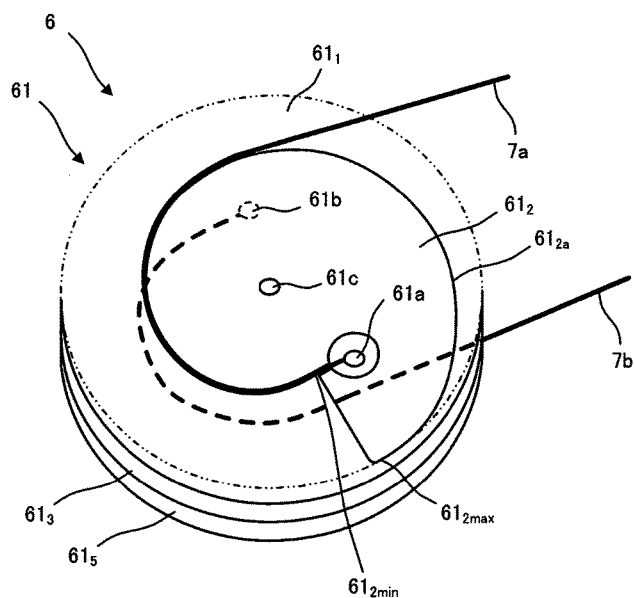
FIG. 2 is illustrative in schematic of the traction part 6 according to the first embodiment of the invention.
Figure 3:
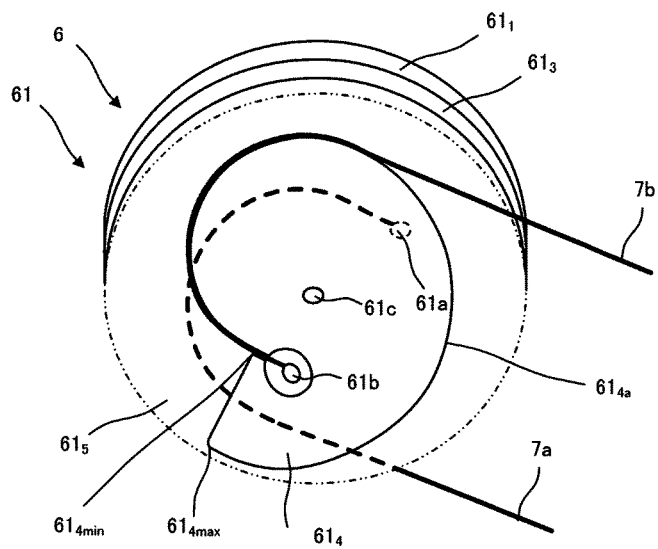
FIG. 3 is a view of FIG. 2 as viewed from the opposite side.

FIG. 2 is a schematic view of the traction part 6 according to the first embodiment of the invention, and FIG. 3 is a view of FIG. 2 as viewed from the opposite side.

The traction part 6 according to the first embodiment of the invention may be a pulley 61 that is driven by the driving part 5 for rotation. The pulley 61 includes a first wire mount 61a to which the other end of a first wire 7a is attached, a second wire mount 61b to which the other end of a second wire 7b is attached, and a center axis 61c that defines the center of rotation.

The pulley 61 includes, in order from one of the axial direction of the center axis 61c to another, a first surface portion $61_1$, a first take-up portion $61_2$, an intermediate portion $61_3$, a second take-up portion $61_4$, and a second surface portion $61_5$. The first surface portion $61_1$, intermediate portion $61_3$ and second surface portion $61_5$ may each be formed of a circular plate.

The first take-up portion $61_2$ is positioned between the first surface potion $61_1$ and the intermediate portion $61_3$ and has a diameter smaller than those of the first surface portion $61_1$ and intermediate portion $61_3$. The first wire mount 61a is formed in the vicinity of the first smallest-diameter site $61_{2min}$ where the outer circumference $61_{2a}$ of the first take-up portion $61_2$ has the smallest diameter.

From the first smallest-diameter site $61_{2min}$ having the smallest diameter to the first largest-diameter site $61_{2max}$ having the largest diameter, the diameter of the outer circumference $61_{2a}$ of the first take-up portion $61_2$ is kept at least constant or incremental or, alternatively not decremental, making sure stable operation of the first take-up portion $61_2$.

Especially from the first smallest-diameter site $61_{2min}$ having the smallest diameter to the first largest-diameter site $61_{2max}$ having the largest diameter, the diameter of the outer circumference $61_{2a}$ of the first take-up portion $61_2$ is preferably kept incremental, and more preferably incremental at a constant rate, making sure more stable operation of the first take-up portion $61_2$.

The second take-up portion $61_4$ is positioned between the intermediate portion $61_3$ and the second surface portion $61_5$ and has a diameter smaller than those of the intermediate portion $61_3$ and second surface portion $61_5$. The second wire mount 61b is formed in the vicinity of the second smallest-diameter site $61_{4min}$ where the outer circumference $61_4a$ of the second take-up portion $61_4$ has the smallest diameter.

From the second smallest-diameter site $61_{4min}$ having the smallest diameter to the second largest-diameter site $61_{4max}$ having the largest diameter, the diameter of the outer circumference $61_4a$ of the second take-up portion $61_4$ is kept at least constant or incremental or, alternatively, not decremental, making sure stable operation of the second take-up portion $61_4$.

Especially from the second smallest-diameter site $61_{4min}$ having the smallest diameter to the second largest-diameter site $61_{4max}$ having the largest diameter, the diameter of the outer circumference $61_4a$ of the first take-up portion $61_4$ is preferably incremental, and more preferably incremental at a constant rate, making sure more stable operation of the first take-up portion $61_4$.

Figure 4:
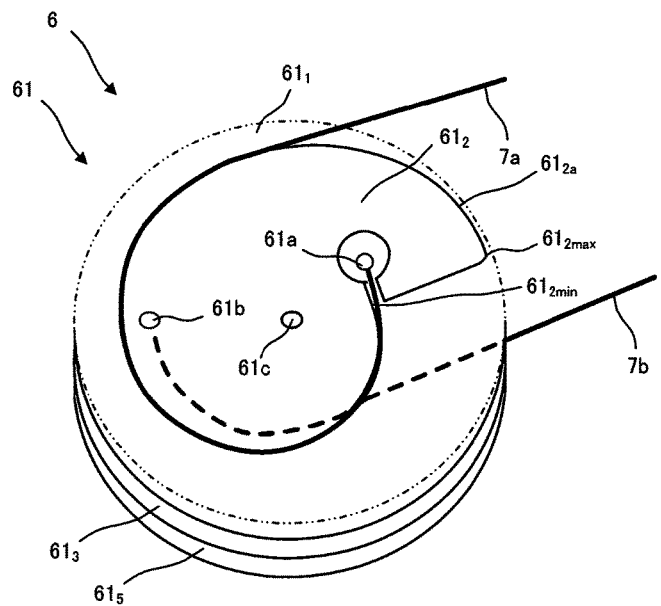
FIG. 4 is illustrative in schematic of one operating state of the traction part 6 according to the first embodiment.
Figure 5:
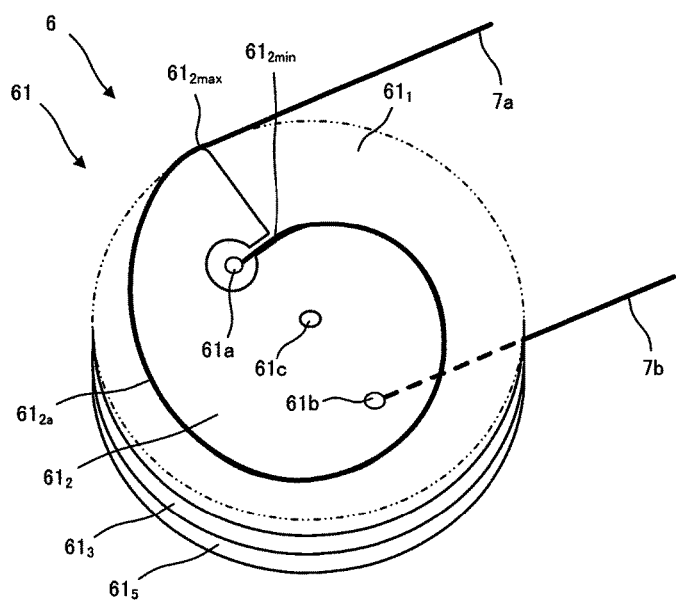
FIG. 5 is illustrative in schematic of an operating state of the traction part 6 according to the first embodiment, which state is different from that of FIG. 4.

FIG. 4 is a schematic view of the operating state of the traction part 6 according to the first embodiment of the invention, and FIG. 5 is a schematic view of the operating state of the traction part 6 according to the first embodiment, which state is different from that of FIG. 4.

As the pulley 61 is rotated in the take-up direction of the first wire 7a from the state of FIG. 2 to the state of FIG. 4, it causes the first wire 7a to be wound on the outer circumference $61_{2a}$ of the first take-up portion $61_2$ and the second wire 7b to let out of the outer circumference $61_4a$ of the second take-up portion $61_4$. In the process of rotation of the pulley 61 from the state of FIG. 2 to the state of FIG. 4, the length of the first wire 7a taken up gets longer than the length of the second wire 7b let out, because the diameter of the outer circumference $61_{2a}$ of the first take-up portion $61_2$ on which the first wire 7a is wound is greater than the diameter of the outer circumference $61_4a$ of the second take-up portion $61_4$ of which the second wire 7b is let out.

Likewise in the process of rotation of the pulley 61 from the state of FIG. 4 to the state of FIG. 5, the length of the first wire 7a wound up gets longer than the length of the second wire 7b let out, because the diameter of the outer circumference $61_{2a}$ of the first take-up portion $61_2$ on which the first wire 7a is wound is greater than the diameter of the outer circumference $61_4a$ of the second take-up portion $61_4$ of which the second wire 7b is let out.

Thus, the movable part 2 can go into operation without any slack in the second wire 7b; the simple structure may be used for unerring operation of the movable part 2 without generation of any dynamic surplus in the wires 7.

Figure 6:
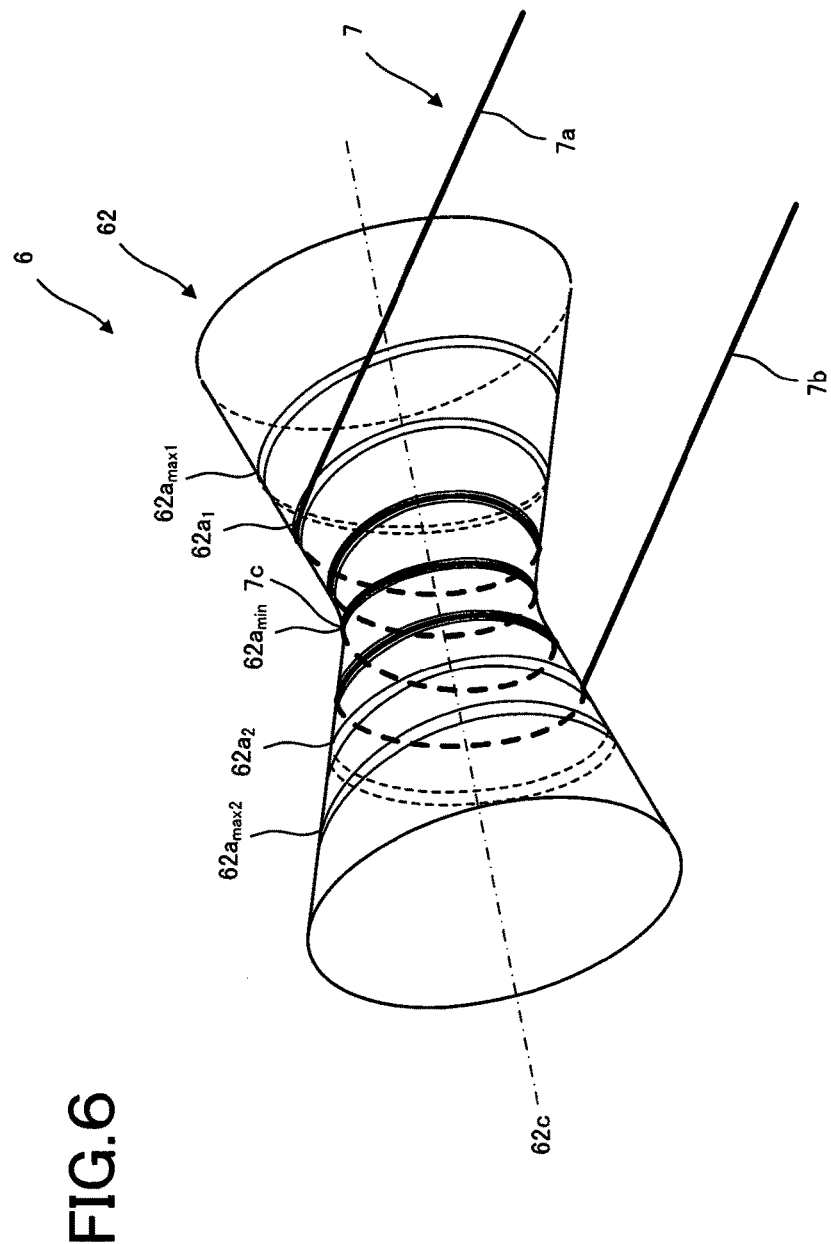
FIG. 6 is illustrative in schematic of the traction part 6 according to the second embodiment of the invention.

FIG. 6 is a schematic view of the traction part 6 according to the second embodiment of the invention.

As shown in FIG. 6, the traction part 6 according to the second embodiment includes a spool-like pulley 62 formed of a cylindrical member that is smaller in diameter near its central axis portion than at both its end portions. The pulley 62 is driven by the driving part 5 for rotation with the center axis 62c as center. The pulley 62 is provided on its outer circumference with a take-up portion 62a formed of a spiral groove.

From the smallest-diameter site $62a_{min}$ positioned at the center of the axial direction and having the smallest diameter to the largest-diameter sites $62a_{max}$ positioned at both ends and having the largest diameter, the diameter of the take-up portion 62a is kept at least constant or incremental or, alternatively, not decremental. Especially from the smallest-diameter site $62a_{min}$ having the smallest diameter to the first largest-diameter site $62a_{max1}$ having the largest diameter on the first wire 7a side and the second largest-diameter site $62a_{max2}$ having the largest diameter on the second wire 7b side, the diameter of the take-up portion 62a is preferably kept incremental, and more preferably incremental at a constant rate.

The take-up portion 62a has the wire 7 wound around. As shown in FIG. 1, the wire 7 is attached at the end to the wire mounts 2a and 2b of the movable part. It is then preferable that an intermediate point 7c of the wire 7 is set in a position of the smallest-diameter site $62a_{min}$ of the pulley 62 such that one half is wound as a first wire portion 7a and the other as a second wire portion 7b.

It is here to be noted that the wire 7 is preferably wound around the take-up portion 62a such that it does not slip thereon. As an example, there may be a guide provided at a given site so as to increase frictional force between the wire 7 and the take-up portion 62a.

The wire 7 may also be divided into two: a first wire 7a and a second wire 7b. With the wire 7 divided into two, it is not required that the ends of two wire portions are attached to the position of the smallest-diameter site $62a_{min}$ of the pulley 62. For instance, the first wire 7a may be attached to the first wire mount (not shown) set in any desired position of the first take-up portion $62a_1$ formed from the smallest-diameter site $62a_{min}$ to the first largest-diameter site $62a_{max1}$, and the second wire 7b may be attached to the second wire mount (not shown) set in any desired position of the second take-up portion $62_{a2}$ formed from the smallest-diameter site $62a_{min}$ to the second largest-diameter site $62a_{max2}$.

The operation of the traction part 6 according to the second embodiment of the invention is now explained.

As the pulley 62 is rotated in the take-up direction of the first wire 7a, it causes the first wire 7a to be wound on the first take-up portion $62a_1$ and the second wire 7b to be let out of the second take-up portion $62_{a2}$. The length of the first wire 7a wound up grows longer than the length of the second wire 7b let out, because the diameter of the first take-up portion $62a_1$ on which the first wire 7a is wound grows large while the diameter of the second take-up portion $62a_2$ of which the second wire 7b is let out becomes short.

Thus, the movable part 2 shown in FIG. 1 can go into operation without any slack in the second wire 7b let out; the simple structure may be used for unerring operation of the movable part 2 without generation of any dynamic surplus in the wire 7.

Figure 7:
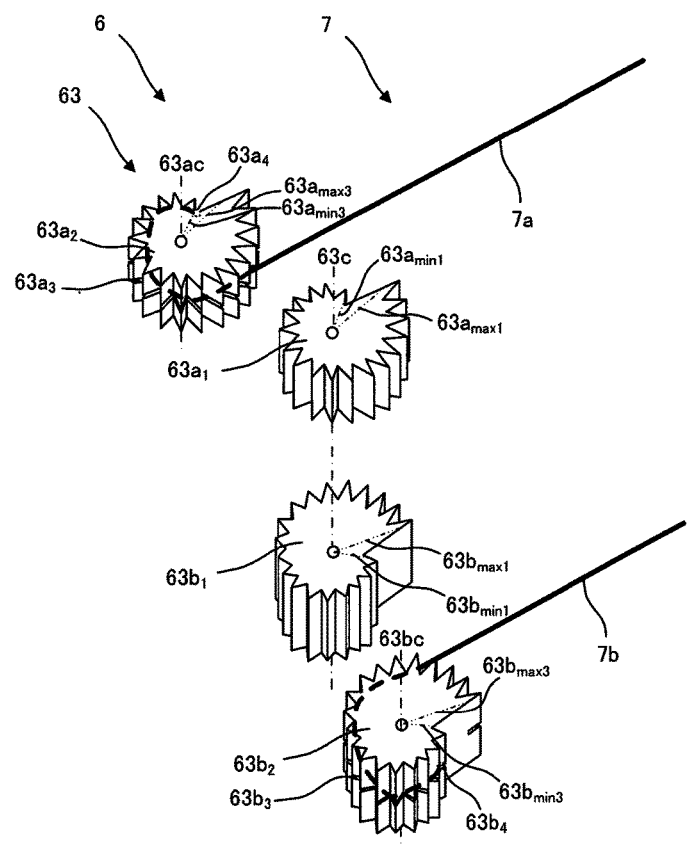
FIG. 7 is illustrative in schematic of the traction part 6 according to the third embodiment of the invention.

FIG. 7 is a schematic view of the traction part 6 according to the third embodiment of the invention.

A deformed gear 63 having varying diameters around its outer circumference is used for the traction part 6 according to the third embodiment, as can be seen from FIG. 7. The first driving gear $63a_1$ and the second driving gear $63b_1$ are driven by the driving part 5 for rotation with a common axis 63c as center.

The diameter of the first driving gear $63a_1$ is kept at least constant or incremental or, alternatively, not decremental from the smallest-diameter site $63a_{min1}$ of the first driving gear having the smallest diameter to the largest-diameter site $63a_{max1}$ of the first driving gear having the largest diameter. Especially from the smallest-diameter site $63a_{min1}$ of the first driving gear having the smallest diameter to the largest-diameter site $63a_{max1}$ of the first driving gear having the largest diameter, the diameter of the first driving gear $63a_1$ is preferably gradually incremental, and more preferably incremental at a constant rate.

The diameter of the second driving gear $63b_1$ is kept at least constant or incremental or, alternatively, not decremental from the smallest-diameter site $63b_{min1}$ of the second driving gear having the smallest diameter to the largest-diameter site $63b_{max1}$ of the second driving gear having the largest diameter. Especially from the smallest-diameter site $63b_{min1}$ of the second driving gear having the smallest diameter to the largest-diameter site $63b_{max1}$ of the second driving gear having the largest diameter, the diameter of the second driving gear $63b_1$ is preferably gradually incremental, and more preferably incremental at a constant rate.

A first driven gear $63a_2$ is in mesh with the first driving gear $63a_1$, and as the first driving gear $63a_1$ is driven, the first driven gear $63a_2$ rotates about a first driven center axis 63ac parallel with the driving center axis 63c. The incremental rate of the diameter of the first driven gear $63a_2$ is determined corresponding to the diameter of the first driving gear $63a_1$. As an example, it is preferable that the first driven gear $63a_2$ engages and rotates with the first driving gear $63a_1$ while the distance from the center axis 63c of the first driving gear $63a_1$ to the first driven center axis 63ac of the first driven gear $63a_2$ remains constant.

The teeth of the first driven gear $63a_2$ are provided with a first take-up portion $63a_3$ including a groove. From the smallest-diameter site $63a_{min3}$ of the first take-up portion having the smallest diameter to the largest-diameter site $63a_{max3}$ of the first take-up portion having the largest diameter, the diameter of the first take-up portion $63a_3$ is kept at least constant or incremental or, alternatively, not decremental. Especially from the smallest-diameter site $63a_{min3}$ of the first take-up portion having the smallest diameter to the largest-diameter site $63a_{max3}$ of the first take-up portion having the largest diameter, the diameter of the first take-up portion $63a_3$ is preferably gradually incremental, and more preferably incremental at a constant rate.

The first driven gear $63a_2$ includes a first wire mount $63a_4$ to which a first wire 7a attached at one end to the movable part 2 shown in FIG. 1 is attached at the other end. The first wire 7a is wound around the first take-up portion $63a_3$.

A second driven gear $63b_2$ is in mesh with the second driving gear $63b_1$, and as the second driving gear $63b_1$ is driven, the second driven gear $63b_2$ rotates about a second driven center axis 63bc parallel with the driving center axis 63c. The incremental rate of diameter of the second driven gear $63b_2$ is determined corresponding to the diameter of the second driving gear $63b_1$. As an example, it is preferable that the second driven gear $63b_2$ engages and rotates with the second driving gear $63b_1$ while the distance from the center axis 63c of the second driving gear $63b_1$ to the second driven center axis 63bc of the second driven gear $63b_2$ remains constant.

The teeth of the second driven gear $63b_2$ are provided with a second take-up portion $63b_3$ including a groove. From the smallest-diameter site $63b_{min3}$ of the second take-up portion having the smallest diameter to the largest-diameter site $63b_{max3}$ of the second take-up portion having the largest diameter, the diameter of the second take-up portion $63b_3$ is kept at least constant or incremental or, alternatively, not decremental. Especially from the smallest-diameter site $63b_{min3}$ of the second take-up portion having the smallest diameter to the largest-diameter site $63b_{max3}$ of the second take-up portion having the largest diameter, the diameter of the second take-up portion $63b_3$ is preferably gradually incremental, and more preferably incremental at a constant rate.

The second driven gear $63b_2$ includes a second wire mount 63b, to which a second wire 7b attached at one end to the movable part 2 shown in FIG. 1 is attached at the other end. The second wire 7b is wound around the second take-up portion $63b_3$.

The operation of the traction part 6 according to the third embodiment of the invention is now explained.

As the first driving gear $63a_1$ is rotated in the take-up direction of the first wire 7a and the second driving gear $63b_1$ is rotated in the direction in which the second wire 7b is let out, it causes the first wire 7a to be wound on the first take-up portion $63a_3$ of the first driven gear $63a_2$ and the second wire 7b to be let out of the second take-up portion $63b_3$ of the second driven gear $63b_2$. The length of the first wire 7a wound up grows longer than the length of the second wire 7b let out, because the diameter of the first take-up portion $63a_3$ on which the first wire 7a is would grows large while the diameter of the second take-up portion $63b_3$ from which the second wire 7b is let out becomes small.

Thus, the movable part 2 shown in FIG. 1 can go into operation without any slack in the second wire 7b let out; the simple structure may be used for unerring operation of the movable part 2 without generation of any dynamic surplus in the wire 7.

Figure 8:
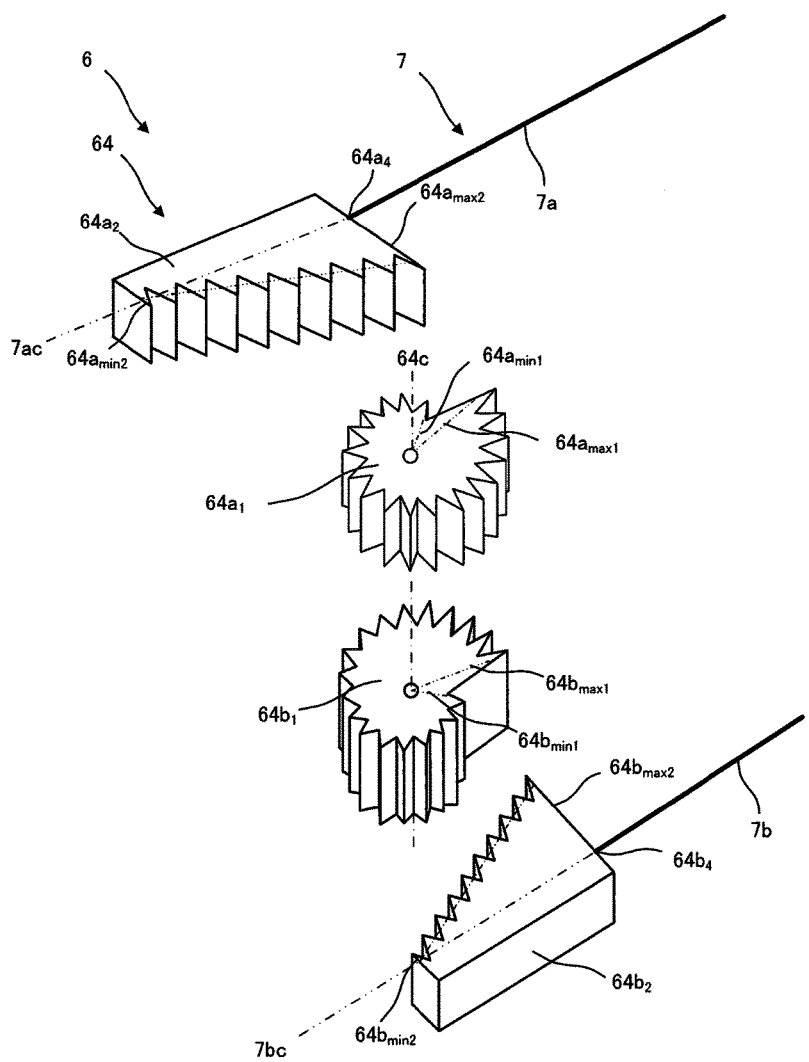
FIG. 8 is illustrative in schematic of the traction part 6 according to the fourth embodiment of the invention.

FIG. 8 is a schematic view of the traction part 6 according to the fourth embodiment of the invention.

As can be seen from FIG. 8, the traction part 6 according to the fourth embodiment is defined by a deformed rack-and-pinion mechanism including a deformed pinion member having varying outer circumference diameters and a rack member having a tilting tooth potion. A first $64a_1$ and a second driving gear $64b_1$, forming the deformed pinion member, are driven by the driving part 5 shown in FIG. 1 for rotation about a common center axis $64c$. A first driven member $64a_2$ and a second driven member $64b_2$, forming the rack member having a tilting tooth portion, are in mesh with the first driving gear $64a_1$ and the second driving gear $64b_1$, respectively.

From the smallest-diameter portion $64a_{min1}$ of the first driving gear having the smallest diameter to the largest-diameter portion $64a_{max1}$ of the first driving gear having the largest diameter, the diameter of the first driving gear $64a_1$ is kept at least constant or incremental or, alternatively, not decremental. Especially from the smallest-diameter portion $64a_{min1}$ of the first driving gear having the smallest diameter to the largest-diameter portion $64a_{max1}$ of the first driving gear having the largest diameter, the diameter of the first driving gear $64a_1$ is preferably gradually incremental, and more preferably incremental at a constant rate.

From the smallest-diameter portion $64b_{min1}$ of the second driving gear having the smallest diameter to the largest-diameter portion $64b_{max1}$ of the second driving gear having the largest diameter, the diameter of the second driving gear $64b_1$ is kept at least constant or incremental or, alternatively, not decremental. Especially from the smallest-diameter portion $64b_{min1}$ of the second driving gear having the smallest diameter to the largest-diameter portion $64b_{max1}$ of the second driving gear having the largest diameter, the diameter of the second driving gear $64b_1$ is preferably gradually incremental, and more preferably incremental at a constant rate.

The first driven member $64a_2$ includes a first wire mount $64a$, to which the first wire $7a$ attached at one end to the movable part 2 (shown in FIG. 1) is attached at the other end. The first driven member $64a_2$ meshes with the first driving gear $64a_1$ and moves linearly in a plane orthogonal to the driving center axis $64c$ as the first driving gear $64a_1$ is driven. As an example, it is preferable that the tooth tilting rate of the first driven member $64a_2$ is compatible with the incremental/decremental rate of diameter of the first driving gear $63a_1$ such that a straight line $7ac$ in the extension direction of the first wire $7a$ lies always in the same position. For this reason, there may be a guide member (not shown) used so as to move the first driven member $64a_2$ on the straight line $7ac$ in the extension direction of the first wire $7a$.

The second driven member $64b_2$ includes a second wire mount $64b$, to which the second wire $7b$ attached at one end to the movable part 2 (shown in FIG. 1) is attached at the other end. The second driven member $64b_2$ meshes with the second driving gear $64b_1$ and moves linearly in a plane orthogonal to the driving center axis $64c$ as the second driving gear $64b_1$ is driven. As an example, it is preferable that the tooth tilting rate of the second driven member $64b_2$ is compatible with the incremental/decremental rate of diameter of the second driving gear $63b_1$ such that a straight line $7bc$ in the extension direction of the second wire $7b$ lies always in the same position. For this reason, there may be a guide member (not shown) used so as to move the second driven member $64b_2$ on the straight line $7bc$ in the extension direction of the second wire $7b$.

The operation of the traction part 6 according to the fourth embodiment of the invention is now explained.

As the first driving gear $64a_1$ and the second driving gear $64b_1$ are rotated in the direction in which the first wire $7a$ is pulled toward the first driven member $64a_2$ side, it causes the second driven member $64b_2$ to be pulled by the second wire $7b$. The length of the first wire $7a$ pulled is longer than the length of the second wire $7b$ let out, because the diameter of the first driving gear $64a_1$ that pulls the first wire $7a$ gets small as it rotates and the diameter of the second take-up portion $63b_3$ from which the second wire $7b$ is let out gets short.

Thus, the movable part 2 shown in FIG. 1 can go into operation without any slack in the second wire $7b$ let out; the simple structure may be used for unerring actuation of the movable part 2 without generation of any dynamic surplus in the wire 7.

Figure 9:
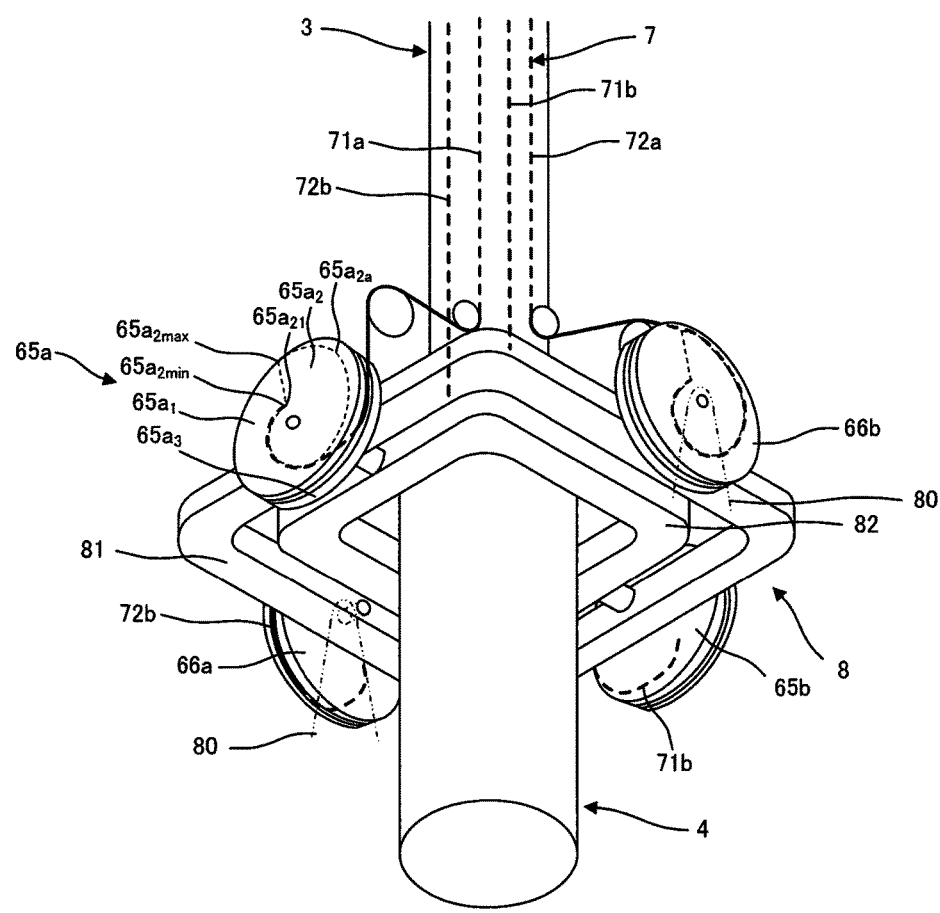
FIG. 9 is illustrative in schematic of the traction part 6 according to the fifth embodiment of the invention.

FIG. 9 is a schematic view of the traction part 6 according to the fifth embodiment of the invention.

As can be seen from FIG. 9, the traction part 6 according to the fifth embodiment has an arrangement wherein one pulley 61 according to the first embodiment shown in FIG. 2 is divided to two portions, each corresponding to one wire 7, and a gimbal mechanism is used for operation of the movable part 2 (shown in FIG. 1) through two degrees of freedom.

According to the fifth embodiment, the traction part 6 includes a first pulley 65a, a second pulley 65b, a third pulley 66a, and a fourth pulley 66b. The first pulley 65a and the second pulley 65b are located in opposite positions. As a first wire $71a$ wound around the first pulley 65a and a second wire $71b$ wound around the second pulley 65b are pushed/pulled, it causes the movable part 2 shown in FIG. 1 to move in the opposite directions.

It is here to be noted that the first pulley 65a and the second pulley 65b and the third pulley 66a and the fourth pulley 66b have a similar structure; only the structure of the first pulley 65a is now explained with no reference to the rest.

In order from one to another of the axial direction of the center axis $65ac$, the first pulley 65a includes a first surface portion $65a_1$, a first take-up portion $65a_2$, and a second surface portion $65a_3$.

The first take-up portion $65_2$ is positioned between the first surface portion $65_1$ and the second surface portion $65a_3$ and has a diameter smaller than those of the first surface portion $65_1$ and the second surface portion $65a_3$, and the first wire take-up portion $65a_{21}$ is formed near the first smallest-diameter site $65a_{2min}$ of the outer circumference $65_{2a}$ of the first take-up portion $65_2$.

From the first smallest-diameter site $65_{2min}$ having the smallest diameter to the largest diameter-site $65_{2max}$ having the largest diameter, the diameter of the outer circumference $65_{2a}$ of the first take-up portion $65_2$ is kept at least constant or incremental or, alternatively, not decremental. Especially from the first smallest-diameter site $65_{2min}$ having the smallest diameter to the largest diameter-site $65_{2max}$ having the largest diameter, the diameter of the outer circumference $65_{2a}$ of the first take-up portion $65_2$ is preferably gradually incremental, and more preferably incremental at a constant rate.

According to the fifth embodiment, the traction part 6 is attached to a gimbal mechanism 8. The gimbal mechanism 8 includes a support member 80, a first frame member 81 rotatably attached to a given axis with respect to the support member 80, and a second frame member 82 rotatably attached to a given axis with respect to the first frame member 81.

The first frame member 81 is supported on a given axis with respect to the support member 80 for swinging movement, and supports the traction member 6 for rotation as well. In the fifth embodiment, the first pulley 65a to the fourth pulley 66b are attached to the first frame member 81 for each 90°. Note here that the first pulley 65a to the fourth pulley 66b are each driven by a driving part (not shown).

The second frame member 82 is positioned inside the first frame member 81, and supported to an axis orthogonal to the axis by which the first frame member 81 is supported on the support member 80 for swinging movement. The second frame member 82 is provided with at least one of the coupler 3 and operating part 4. Accordingly, the coupler 3 and operating part 4 are capable of going into operation through 2 degrees of freedom with respect to the support member 80.

The wires 7 wound around the first pulley 65a to the fourth pulley 66b are guided to the movable part 2 through the coupler 3 by way of a pulley or guide and so on for changing direction.

Referring here to the traction balance adjustment mechanism 1 according to the fifth embodiment, as the first pulley 65a is rotated in a direction of taking up the first wire 71a, it causes the first wire 71a to be wound around the outer circumference $65a_{2_a}$ of the first take-up portion $65a_2$ and the second wire 71b to be let out of the second pulley 65b. In this case, the length of the first wire 71a wound gets longer than the length of the second wire 7b let out, because the diameter of the outer circumference $65a_{2_a}$ of the first take-up portion $65a_2$ around which the first wire 71a is wound grows greater than the diameter of the outer circumference of the second take-up portion (not shown) of which the second wire 71b is let out.

It is thus possible to put the movable part 2 in operation with no slack in the second wire 71b let out; the simple structure can be used for improved and unerring operation of the movable part 2 with no generation of dynamic surplus in the wire 7.

It is here to be appreciated that the first pulley 65a, second pulley 65b, third pulley 66a and fourth pulley 66b are similar in structure; so the respective wires 7 may be put into operation much in the same manner too.

The manipulator 10 according to the embodiment described herein is now explained.

Figure 10:
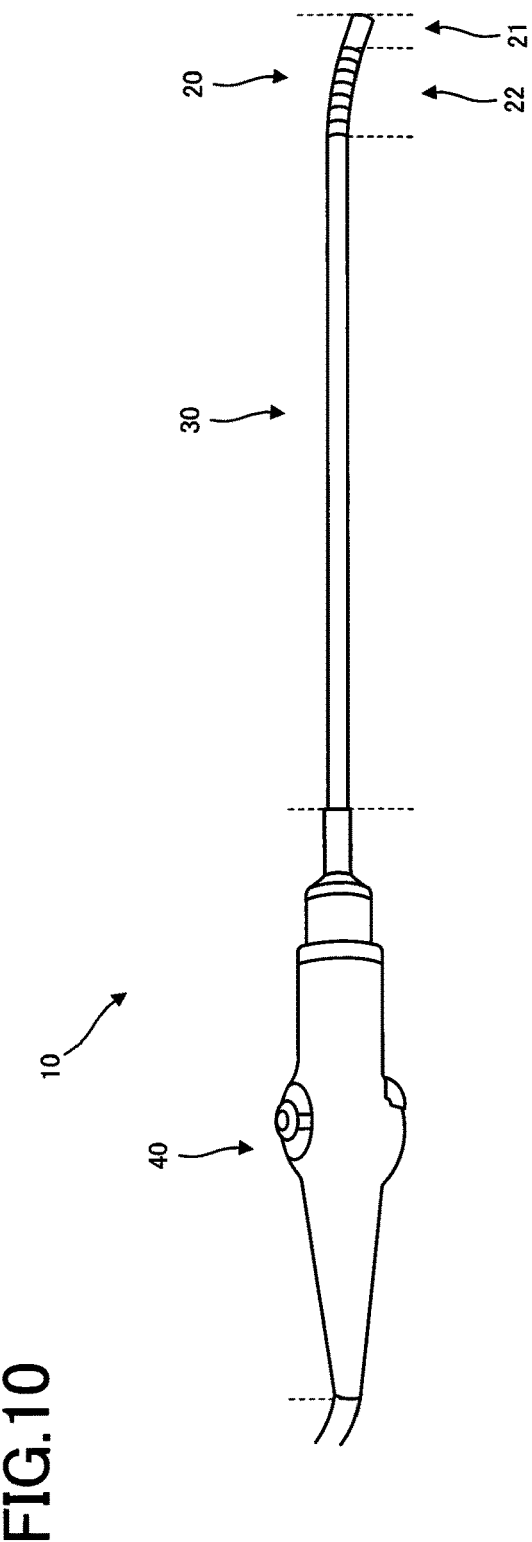
FIG. 10 is illustrative in schematic of the manipulator 10 according to one embodiment of the invention.

FIG. 10 is a schematic view of the manipulator 10 according to the embodiment described herein.

The manipulator 10 according to the embodiment described herein includes a movable part 20, a coupler 30, and an operating part 40. The manipulator 10 includes the movable part 20 on the distal-end side and the operating part 40 on the proximal-end side. Inserted through the body cavity, the movable part 20 includes, in order from the distal-end side, a distal-end portion 21 and a curving portion 22. Coupling the movable part 20 to the operating part 40, the coupler 30 has a wire, etc. built inside. The operating part 40 operates movement or the like of the movable part 20.

Figure 11:
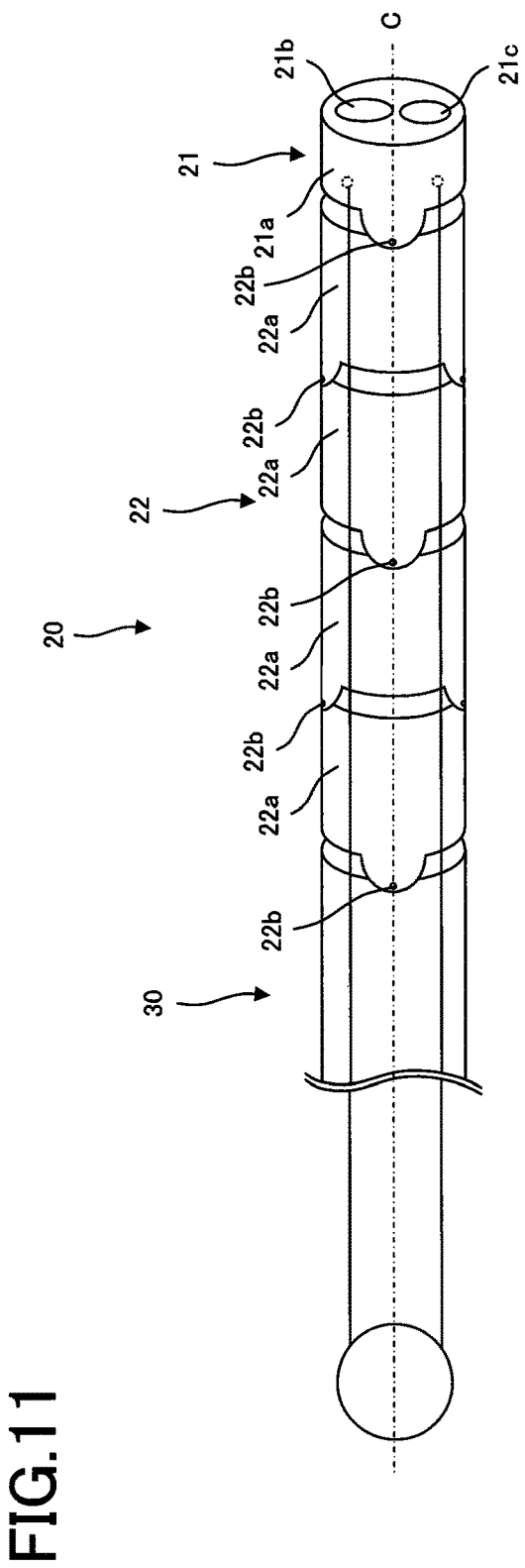
FIG. 11 is an enlarged view of the movable part 20 in the manipulator 10 according to one embodiment of the invention.

FIG. 11 is an enlarged view of the movable part 20 in the manipulator 10 according to the embodiment described herein.

As an example, the manipulator 10 according to the embodiment described herein makes up an endoscope. The distal-end portion 21 includes an columnar treatment portion 21a mounted on the distal end of the manipulator 10, a treatment tool 21b built in the treatment portion 21a, and an imaging portion 21c. Note here that the treatment tool 21b may be forceps, a electric scalpel, etc. for applying treatments to the subject of interest. The imaging portion 21c is used for imaging the subject of interest. There may be a lighting portion (not shown) for lighting the subject of interest.

The curving portion 22 includes substantially columnar articulating pieces 22a and a joint portion 22b adapted to couple adjoining articulating pieces 22a in a rotatable manner within a given angle range. As depicted in FIG. 11, a set of adjoining articulating pieces 22a and joint portion 22b is preferably rotated 90° and located about the axis of the curving portion 22 extended in a straight line, i.e., the center axis C of the coupler 30.

The distal-end portion 21 is attached to the most distal articulating piece 22a of the curving portion 22 by way of the joint portion 22b, and the articulating piece 22a positioned on the most proximal end side of the curving portion 22 is coupled to the coupler 30 by way of the joint portion 22b.

It is here to be noted that the movable part 20 is not limited to the structure; so it may be modified in various fashions.

As the operating part 40 in the manipulator 10 according to the embodiment described herein is operated by an operator, it cause one of the wires 7 wound around the traction part 6 shown in FIG. 1 to be hauled, and the movable part 20 is curved in a direction of the wire 7 being hauled so that the distal-end portion 21 can be pointed to the subject of interest.

The surgical system 90 according to the embodiment described herein is now explained as an example of the manipulator system to which the manipulator 10 according to the embodiment described herein is applied.

Figure 12:
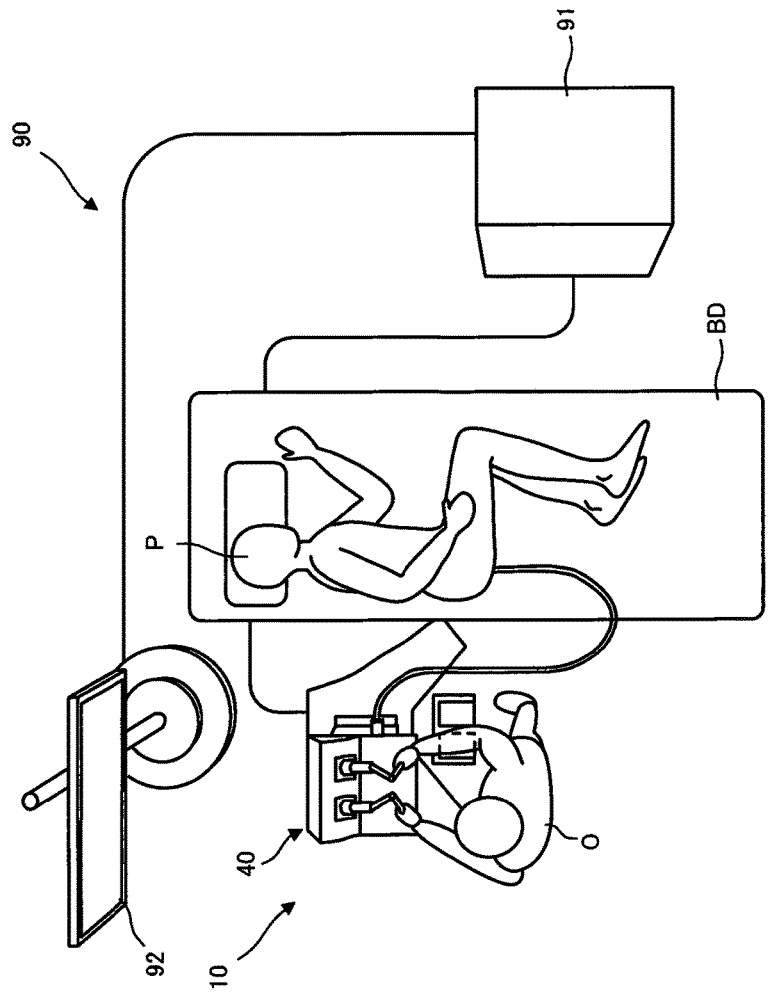
FIG. 12 is illustrative of one example of the manipulator system according to one embodiment of the invention.
Figure 13:
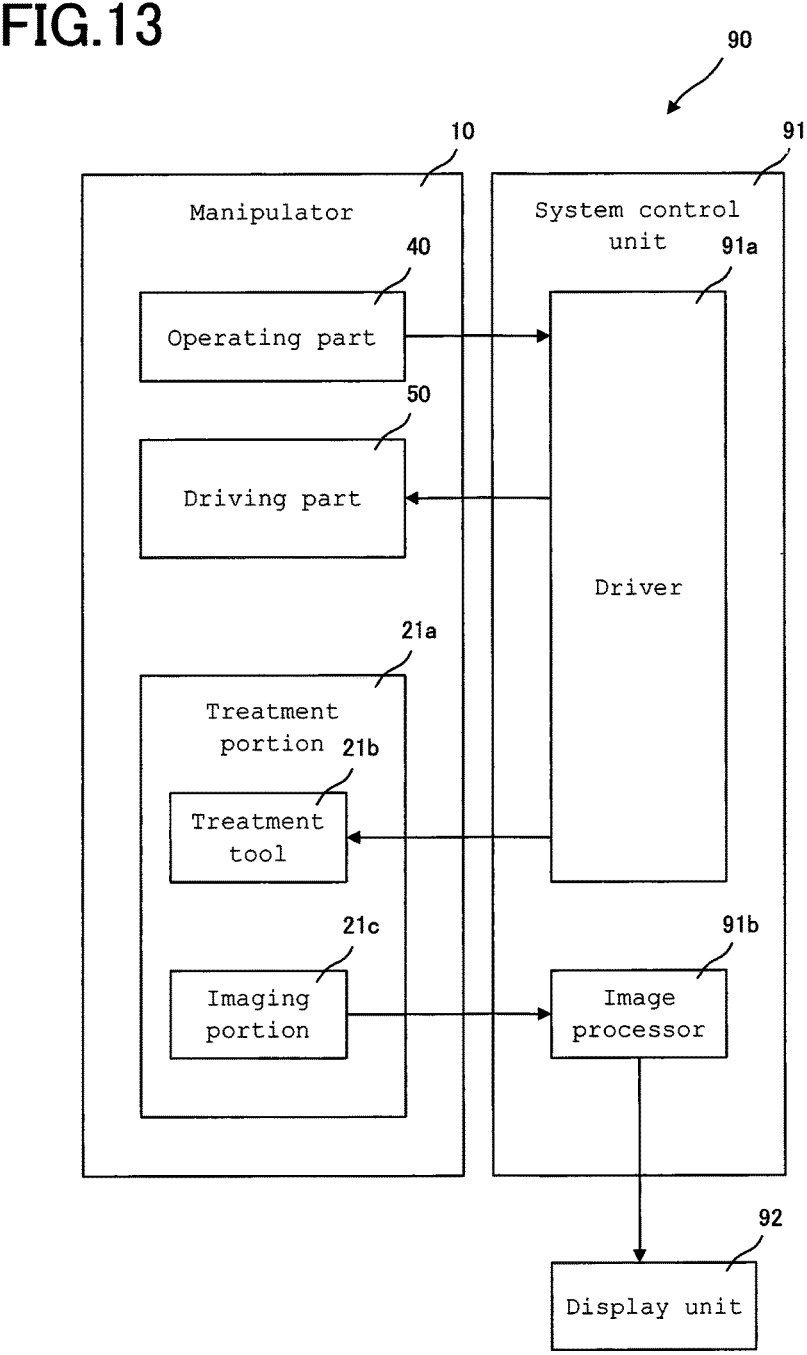
FIG. 13 is a block diagram for one example of the manipulator system according to one embodiment of the invention.

FIG. 12 is illustrative of the surgical system 90 to which the manipulator 1 according to the embodiment described herein is applied, and FIG. 13 is illustrative in configuration of the surgical system 90 to which the manipulator 1 according to the embodiment described herein is applied.

Applied to the surgical system 90 according to the embodiment described herein is the manipulator 10 shown in FIG. 12. The surgical system 90 includes an operating part 40 operated by an operator O, a manipulator 10 that is capable of being inserted through the body of a patient P lying on an operating table BD, that is, a soft organ such as the large intestine or the like and includes a movable part 20 provided at the distal end with a treatment tool 21a shown in FIG. 11 like an endoscope, a control unit 91 for controlling the manipulator 10, and a display unit 92 for displaying an image acquired through an imaging unit 21c of an endoscope built in the manipulator 10 or the like.

As depicted in FIG. 12, the operating part 40 includes a pair of operating handles attached to an operating base, a footswitch or the like located on the surface of the floor. The operating part 40 may have a multi-joint structure. The operational angle of the operating part 40 is acquired by an angle acquisition device such as an encoder, and in response to the thus obtained signal, as depicted in FIG. 13, the control unit 91 actuates the treatment tool 21b or the like located at the distal end of the treatment portion 21a or the like by way of a driver 91a.

An image acquired through the imaging unit 21c is produced out to an image processor 91b in the control unit 91. The image processed by the image processor 91b is produced as a screen display on the display unit 92, and the operator O operates the manipulator 10 while viewing the image appearing on the display unit 92.

Such surgical system 90 does not only have an advantage of the traction balance adjustment mechanism 1 but is also capable of producing an unerring image display asked for by the operator, resulting in more unerring operation of the manipulator 10 by the operator.

Such traction balance adjustment mechanism 1 as explained with reference to the embodiment described herein includes the movable part 2 that operates through at least one degree of freedom, the wires 7 connected to the movable part 2, and the traction part 6 adapted to pull one of the wires 7 and push out the other, wherein the length of one wire 7 pulled by the traction part 6 is longer than that length of the other wire 7 pushed out. It is thus possible to put the movable part 2 into unerring operation with no generation of any dynamic surplus in the wires 7.

With the traction balance adjustment mechanism 1 according to the embodiment described herein, it is possible to put the movable part 2 into stable operation, because the amount of change in the length of one wire 7 pulled by the traction part 6 is kept constant or incremental.

With the traction balance adjustment mechanism 1 according to the embodiment described herein, it is possible to put the movable part 2 into more stable operation, because the amount of change is constantly incremental.

With the traction balance adjustment mechanism 1 according to the embodiment described herein, it is possible to put the movable part 2 into more stable operation, because the amount of change is incremental at a constant rate.

In the traction balance adjustment mechanism 1 according to one embodiment of the invention, the traction part 6 includes the pulleys 61 and 62 that are capable of rotating with respect to a given axis, wherein the pulley 61 includes the helical take-up portions $61_2$, $61_4$, $62a_1$ and $62a_2$ around which the wire 7 is wound, and which have the smallest-diameter sites $61_{2min}$, $61_{4min}$ and $62a_{min}$ having the shortest distance from the axes $61c$ and $62c$ and the largest-diameter sites $61_{2max}$, $61_{4max}$, $62a_{max1}$ and $62a_{max2}$ having the longest distances from the axes $61c$ and $62c$. Accordingly, the simple structure can be used to put the movable part 2 into unerring operation with no generation of any dynamic surplus in the wire 7.

In the traction balance adjustment mechanism 1 according to the embodiment described herein, the wire 7 includes at least one pair of first wire $7a$ and second wire $7b$, the movable part 2 includes a first connector $2a$ that makes a connection to one end of the first wire $7a$ and a second connector $2b$ that makes a connection to one end of the second wire $7b$, the pulley 61 includes a first take-up portion $61_2$ which has a first largest-diameter site $61_{2max}$ and around which the first wire $7a$ is wound and a second take-up portion $61_4$ which has a second largest-diameter site $61_{4max}$ and around which the second wire $7b$ is wound, and the smallest-diameter sites $61_{2min}$ and $61_{4min}$ include a first smallest-diameter site $61_{2min}$ adjacent to a first mount $61a$ to which the other end of the first wire $7a$ wound around the first take-up portion $61_2$ is attached and a second smallest-diameter site $61_{4min}$ adjacent to a second mount $61b$ to which the other end of the second wire $7b$ around the second take-up portion $61_4$ is attached. Thus, the simple structure can be used for rapid removal of any dynamic surplus in the wire 7 thereby making sure unerring operation of the wire 7.

In the traction balance adjustment mechanism 1 according to the embodiment described herein, the traction part 6 includes driving gears $63a_1$ and $63b_1$ that are rotatable with respect to a given axis and first driven gear $63a_2$ and second driven gear $63b_2$ in mesh with the driving gears $63a_1$ and $63b_1$, respectively; the wire 7 includes at least one pair of first wire $7a$ and second wire $7b$; and the movable part 2 includes a first connector $2a$ that makes a connection to one end of the first wire $7a$ and a second connector $2b$ that makes a connection to one end of the second wire $7b$, wherein the first driven gear $63a_2$ includes a first take-up portion $63a_3$ around which the first wire $7a$ is wound, the second driven gear $63b_2$ includes a second take-up portion $63b_3$ around which the second wire $7b$ is wound, the first take-up portion $63a_3$ includes a first smallest-diameter site $63a_{min3}$ to which the other end of the first wire $7a$ is attached and a first largest-diameter site $63a_{max3}$ positioned on the outermost circumference, and the second take-up portion $63b_3$ includes a second smallest-diameter site $63b_{min3}$ to which the other end of the second wire $7b$ is attached and a second largest-diameter site $63b_{max3}$ positioned on the outermost circumference. Thus, the simple structure can be used to put the wire 7 into unerring operation with no generation of any dynamic surplus in the wire 7.

In the traction balance adjustment mechanism 1 according to the embodiment described herein, the traction part 6 includes driving gears $64a_1$ and $64b_1$ that are rotatable with respect to a given axis $64c$ and first driven member $64a_2$ and second driven member $64b_2$ in mesh with the driving gears $64a_1$ and $64b_1$, respectively; the wire 7 includes at least one pair of first wire $7a$ and second wire $7b$; and the movable part 2 includes a first connector $2a$ that makes a connection to one end of the first wire $7a$ and a second connector $2b$ that makes a connection to one end of the second wire $7b$, wherein the first driven member $64a_2$ includes a first mount $64a_4$ to which the first wire $7a$ is attached, the second driven member $64b_2$ includes a second mount $63b_4$ to which the second wire $7b$ is attached, the driving gears $64a_1$ and $64b_1$ include a first driving gear $64a_1$ provided with a first driving smallest-diameter site $64a_{min1}$ and a first driving largest-diameter site $64a_{max1}$ and a second driving gear $64b_1$ provided with a second driving smallest-diameter site $64b_{min1}$ and a second driving largest-diameter site $64b_{max1}$, the tooth tilting rate of the first driven member $64a_2$ is compatible with the incremental/decremental rate of diameter of the first driving gear $64a_1$ such that the straight line in the direction of extension of the first wire $7a$ lies always in the same position, and the tooth tilting rate of the second driven member $64b_2$ is compatible with the incremental/decremental rate of diameter of the second driving gear $64b_1$ such that the straight line in the direction of extension of the second wire $7b$ lies always in the same position. Thus, the simple structure can be used to put the wire 7 into unerring operation with no generation of any dynamic surplus in the wire 7.

The traction balance adjustment mechanism 1 according to the embodiment described herein includes a coupler 3 that supports the movable part 2 in a rotatable manner, and a gimbal mechanism including a support member 80 for supporting the coupler 3, a first frame member 81 that is rotatably attached to a given first axis with respect to the support member 80 and a second frame member 82 that is rotatably attached to a given second axis with respect to the first frame member 81, the second axis being different from the first axis, wherein the traction part 6 is attached to the first frame member 81. Thus, the simple structure can be used to put the wire 7 into unerring operation with enhanced operability but with no generation of any dynamic surplus in the wire 7.

The manipulator 10 according to the embodiment described herein includes a driving part 50 that drives a traction part 6, an operating part 40 that puts the driving part 50 into operation to operate the orientation of the movable part 20, and a traction balance adjustment mechanism 1. It is thus possible not only to have an advantage of the traction balance adjustment mechanism 1 but also to rapidly curve the movable part 20 in the direction of traction of the wire 7 so that the distal-end portion 21 can be unerringly directed to the subject of interest.

The surgical system 90 according to the embodiment described herein includes a manipulator 10, a system control unit 91 that controls the manipulator 10, and a display unit 92 that displays an image acquired by the manipulator 10, wherein the manipulator 10 includes an imaging unit 21c, and the system control unit 91 displays an image through the imaging unit 21c on a display unit 92. It is thus possible not only to have an advantage of the traction balance adjustment mechanism 1 but also to provide an unerring image asked for by the operator, making it for the operator to put the manipulator 10 into more unerring operation.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Traction balance adjustment mechanism
2: Movable part
3: Coupler
4: Operating part
5: Driving part
6: Traction part
61, 62: Pulley
63: Deformed gear
64: Guide for interconnecting pulleys
7: Wire (power transmission member)
8: Surplus absorber
10: Manipulator
20: Movable part
21: Distal-end portion
22: Curving portion
30: Coupler
40: Operating part
90: Surgical system (manipulator system)
91: Control unit
92: Display unit

The invention claimed is:

1. A traction balance adjustment mechanism comprising:
a movable part that moves with respect to a cylindrical coupler through at least one degree of freedom;
a first wire and a second wire that are connected to an inside of the movable part for transmission of power to the movable part; and
an operating part that is provided at a proximal end of the coupler to operate the movable part by the first wire and the second wire, and
a pulley provided on the operating part wherein the pulley rotates with respect to a center axis of the pulley, wherein:
the pulley comprises:
a first take-up portion that is mounted on a first surface portion defining a vertical plane with respect to the center axis of the pulley to wind up the first wire, and
a second take-up portion that is mounted on a second surface portion provided parallel with the first surface portion to wind up the second wire, wherein the first take-up portion includes a first smallest diameter site where a distance from the center axis to an outer diameter of the first take-up portion is shortest and a first largest diameter site where a distance from the center axis to the outer diameter of the first take-up portion is longest, and
the second take-up portion includes a second smallest diameter site where a distance from the center axis to an outer diameter of the second take-up portion is shortest and a second largest diameter site where a distance from the center axis to the outer diameter of the second take-up is longest, wherein:
an amount of the first wire wound up by the first take-up portion is larger than an amount of the second wire fed by the second take-up portion toward the movable part,
the outer diameter of the first take-up portion is gradually incremental from the first smallest diameter site to the first largest diameter site, and
the outer diameter of the second take-up portion is gradually incremental from the second smallest diameter site to the second largest diameter site.

2. A traction balance adjustment mechanism according to claim 1, wherein:
the movable part includes a first connector that makes a connection to one end of the first wire and a second connector that makes a connection to one end of the second wire, the movable part further includes a first mount which is mounted on the first take-up portion and to which the other end of the first wire provided at a given distance from the center axis toward the outer diameter of the first take-up portion is attached and a second mount which is mounted on the second take-up portion and to which the other end of the second wire provided at a given distance from the center axis is attached.

3. A manipulator comprising:
a driving part for driving the pulley;
an operating part for operating the driving part to operate an orientation of the movable part; and
a traction balance adjustment mechanism according to claim 1.

4. A manipulator system comprising:
a manipulator according to claim 3;
a system controller for controlling the manipulator; and
a display unit for displaying an image acquired through the manipulator;
wherein the manipulator includes an endoscope, and the system controller is adapted to display an image acquired through the endoscope on the display unit.

5. A traction balance adjustment mechanism according to claim 1, wherein in a point symmetrical position with respect to a center point of an intermediate portion sandwiched between the first take-up portion and the second take-up portion at which point the outer diameter of the intermediate portion intersects the center axis, the first and second take-up portions are located on the first and second surface portions, respectively.

* * * * *